US011534120B2

(12) United States Patent
Garlow et al.

(10) Patent No.: US 11,534,120 B2
(45) Date of Patent: Dec. 27, 2022

(54) LINE SCANNER IMAGING DEVICE, SYSTEM, AND METHODS

(71) Applicant: Medtronic Navigation, Inc., Louisville, CO (US)

(72) Inventors: David A. Garlow, Lynnfield, MA (US); Elizabeth A. Levasseur, New Boston, NH (US)

(73) Assignee: Medtronic Navigation, Inc., Louisville, CO (US)

( * ) Notice: Subject to any disclaimer, the term of this patent is extended or adjusted under 35 U.S.C. 154(b) by 222 days.

(21) Appl. No.: 16/901,877

(22) Filed: Jun. 15, 2020

(65) Prior Publication Data

US 2021/0386388 A1 Dec. 16, 2021

(51) Int. Cl.
*A61B 6/00* (2006.01)
(52) U.S. Cl.
CPC .......... *A61B 6/4405* (2013.01); *A61B 6/4441* (2013.01); *A61B 6/54* (2013.01); *A61B 6/587* (2013.01)
(58) Field of Classification Search
CPC ....... A61B 6/54; A61B 6/4441; A61B 6/5241; A61B 6/505; A61B 6/587; A61B 6/4476; A61B 6/4482; A61B 6/4429; A61B 6/4405; A61B 6/547; A61B 6/56; A61B 5/055; A61B 6/4085; A61B 6/485; A61B 6/032; A61B 6/4411; A61B 6/4447; A61B 6/04; A61B 6/035; A61B 6/4494; A61B 6/545; A61B 6/0407; A61B 6/5205; A61B 6/105; A61B 6/4435; A61B 6/4275; A61B 6/44; A61B 6/06; A61B 6/4035; A61B 6/482;

(Continued)

(56) References Cited

U.S. PATENT DOCUMENTS 5,386,453 A * 1/1995 Harrawood .......... A61B 6/4476
378/198
5,745,544 A 4/1998 Mazess
(Continued)

FOREIGN PATENT DOCUMENTS

CN 108671418 10/2018
DE 102015207736 11/2016
(Continued)

OTHER PUBLICATIONS

International Search Report and Written Opinion for International (PCT) Patent Application No. PCT/US2021/037227, dated Sep. 23, 2021, 15 pages.

(Continued)

*Primary Examiner* — Irakli Kiknadze
(74) *Attorney, Agent, or Firm* — Sheridan Ross P.C.

(57) ABSTRACT

An imaging device for obtaining long-film images of an anatomical element of a patient or of another object includes a wheeled base comprising an elongate track; a trolley comprising a base portion slidably connected to the elongate track and an upper portion rotatably connected to the base portion, the trolley slidable along the elongate track a distance of at least 40 cm; a C-shaped arm defining a semi-circle about a C-shaped arm axis, the C-shaped arm rotatably supported by the upper portion of the trolley; a source fixedly secured to the C-shaped arm; and a detector fixedly secured to the C-shaped arm opposite the source.

20 Claims, 9 Drawing Sheets

(58) Field of Classification Search
CPC ......... A61B 6/542; A61B 6/481; A61B 6/504; A61B 34/20; A61B 6/12; A61B 2034/2051; A61B 2090/3762; A61B 2034/2055; A61B 2034/2059; A61B 6/4452; A61B 6/4464; A61B 90/37; A61B 6/462; A61B 6/582; A61B 6/0487; A61B 6/583; A61B 6/102; A61B 6/50; A61B 6/4233; A61B 6/4078; A61B 6/461; A61B 6/466; A61B 6/465; A61B 6/0464; A61B 6/501; A61B 6/4291; A61B 6/08; A61B 6/4417; A61B 6/487; A61B 6/4488; A61B 6/548; A61B 6/0492; A61B 6/025; A61B 6/541; A61B 6/527; A61B 6/00; H02G 11/006; B60B 33/066; A61M 5/007; G01T 1/1606; G01R 33/4812
USPC .................. 378/4, 20, 102, 193–198, 11, 17
See application file for complete search history.

(56) References Cited

U.S. PATENT DOCUMENTS

| | | | |
|---|---|---|---|
| 6,461,039 | B1 | 10/2002 | Klotz et al. |
| 6,609,826 | B1 | 8/2003 | Fujii et al. |
| 7,300,205 | B2 | 11/2007 | Grady |
| 7,338,207 | B2 | 3/2008 | Gregerson et al. |
| 7,354,196 | B2 | 4/2008 | Boese et al. |
| 8,303,181 | B2 | 11/2012 | Sukovic et al. |
| 10,390,777 | B2 | 8/2019 | Risher-Kelly et al. |
| 10,799,194 | B2 * | 10/2020 | Stanton .................. A61B 6/035 |
| 2008/0013691 | A1 | 1/2008 | Gregerson et al. |
| 2017/0143288 | A1 | 5/2017 | Packard et al. |
| 2017/0245826 | A1 | 8/2017 | Kasaoka |
| 2018/0289339 | A1 | 10/2018 | Fortuna et al. |
| 2019/0029629 | A1 | 1/2019 | Johnson et al. |
| 2019/0099140 | A1 | 4/2019 | Garlow et al. |
| 2019/0099141 | A1 | 4/2019 | Garlow et al. |
| 2019/0150865 | A1 * | 5/2019 | Johnson ............... A61B 6/4441 |

FOREIGN PATENT DOCUMENTS

| | | |
|---|---|---|
| EP | 0713676 | 5/1996 |
| EP | 1779783 | 5/2014 |
| EP | 3367901 | 8/2019 |

OTHER PUBLICATIONS

"Alphenix Biplane—Multi-Access Biplane System," Canon Medical US, Jan. 8, 2019, 14 pages [retrieved online from: www.youtube.com/watch?v=GWQmyhBFUBI].

"OEC Elite™ Premium Digital Mobile C-arm Technical Data," General Electric Company, 2016, 2 pages.

* cited by examiner

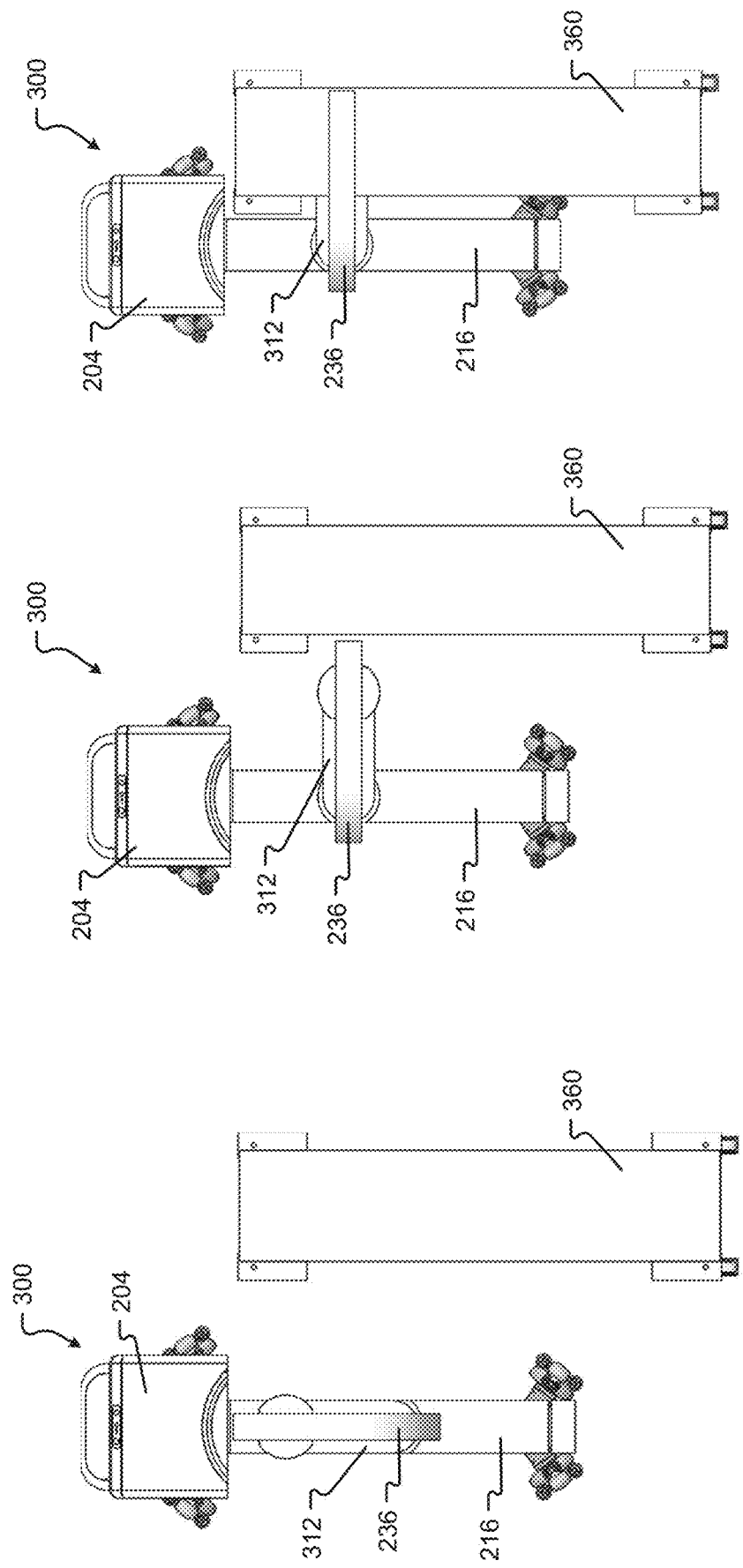

LINE SCANNER IMAGING DEVICE, SYSTEM, AND METHODS

FIELD

The present technology is related generally to imaging devices and, more particularly, to medical imaging devices capable of long-film line scanning.

BACKGROUND

O-arms using breakable gantries or doors are often utilized to obtain an image around a full 360° of an object. The door of such O-arms can be opened to allow the O-arm to be positioned around a patient (and, for example, a table or bed on which the patient rests, typically in a prone position). The door can then be closed so that the O-arm encircles the patient entirely, and one or more imaging sensors can "spin" around the O-arm to achieve a full 360° image of the patient or a portion thereof.

O-arms are also able to generate a 2-dimensional image for spine applications, but are limited to 30 cm of travel along the Z-axis (i.e., in the superior-inferior direction). Where visualization of an anatomical element over a greater distance is desired, larger machines such as CT or MRI scanners may be utilized.

SUMMARY

O-arms are heavy and bulky, and correspondingly difficult to maneuver. O-arms are also expensive. Because they are designed and built to enable 360° imaging of an object, O-arms represent an over-engineered solution to the problem of taking 2-dimensional, long-film images. Even so, conventional O-arms are incapable of obtaining long-film images longer than 30 cm, and thus cannot be used in many instances to obtain a full long-film image of the human spine.

Although CT and MM machines are capable of obtaining long-film images longer than 30 cm, such machines are large, fixed, and also expensive. CT and MRI machines are capable of far more than taking 2-dimensional images, and therefore also represent an over-engineered solution to the problem of obtaining such images.

A C-shaped arm as disclosed herein is an imaging device with an X-ray emission device fixed at one end of a semi-circular arm and an X-ray detector device fixed at an opposite end of the semi-circular arm, approximately 180° of angular distance apart from the X-ray emission device. As a result, C-shaped arms are useful for obtaining 2D images.

Line scanner imaging devices and systems according to embodiments of the present disclosure provide a portable, cost-effective, appropriate solution for obtaining long-film images as long as 60 cm or more, and are thus able to image an entire human spine. Such devices and systems are considerably less bulky than O-arms as well as larger machines such as CT and MM scanners, and can be both readily transported through a healthcare facility to a patient, and easily maneuvered into position relative to the patient. In some embodiments, line scanner imaging devices and systems according to the present disclosure are capable of taking images in multiple directions, including the lateral direction and the anterior-posterior direction An imaging device according to one embodiment of the present disclosure comprises: a wheeled base comprising an elongate track; a trolley comprising a base portion slidably connected to the elongate track and an upper portion rotatably connected to the base portion, the trolley slidable along the elongate track a distance of at least 40 cm; a C-shaped arm defining a semi-circle about a C-shaped arm axis, the C-shaped arm rotatably supported by the upper portion of the trolley; a source fixedly secured to the C-shaped arm; and a detector fixedly secured to the C-shaped arm opposite the source.

The upper portion may be rotatable relative to the base portion about a first axis perpendicular to the elongate track. The upper portion may be configured to selectively rotate the C-shaped arm about the C-shaped arm axis. The trolley may further comprise an intermediate arm rotatable between a first position parallel to the elongate track and a second position perpendicular to the elongate track. The wheeled base may comprise a plurality of omnidirectional wheels. The wheeled base may comprise a plurality of powered wheels and a controller for selectively activating the powered wheels to move the wheeled base relative to a stationary object. The trolley may be slidable along the elongate track a distance of at least 60 cm.

The imaging device may further comprise a processor and a memory. The memory may store instructions for execution by the processor that, when executed, cause the processor to: transmit a first signal that causes the upper portion to rotate relative to the base portion; transmit a second signal that causes the C-shaped arm to rotate about the C-shaped arm axis; activate the source and the detector; and transmit a third signal that causes the trolley to slide along a length of the elongate track in a first direction. The memory may store additional instructions for execution by the processor that, when executed, further cause the processor to transmit a fourth signal that causes the wheeled base to automatically move in a second direction opposite the first direction.

The imaging device may further comprise a sensor for determining a position of the C-shaped arm relative to a stationary object.

An imaging system according to another embodiment of the present disclosure comprises: a housing; an elongate member extending from the housing; a mount slidably secured to the elongate member; a C-shaped arm defining a C-shaped arm axis and movably attached to the mount, the C-shaped arm rotatable on the mount about a first axis perpendicular to the elongate member and about the C-shaped arm axis, the C-shaped arm comprising an imaging tool; and a control system configured to selectively cause the mount to slide along the elongate member and the C-shaped arm to rotate relative to the mount, and to selectively activate the imaging tool.

The housing and the elongate member may be supported by a plurality of wheels. At least some of the plurality of wheels may be powered, and the control system may be further configured to selectively activate the powered wheels. The C-shaped arm may be movable between a storage configuration, in which the C-shaped arm and the elongate member are co-planar, and an operating position, in which the C-shaped arm defines a first plane and the elongate member defines a second plane perpendicular to the first plane. The mount may be slidable along the elongate member by a distance of at least 50 cm.

A method of operating an imaging device according to yet another embodiment of the present disclosure comprises: aligning a linear track of an imaging device with an object to be imaged, the object elongated in a longitudinal direction; rotating a C-shaped arm of the imaging device so that an axis defined by the C-shaped arm extends through the object in the longitudinal direction; activating a source and detector secured to the C-shaped arm; and moving the C-shaped arm along the linear track in a first direction while the source and detector are activated to yield a first elongate image of the object.

The method may further comprise: rotating the C-shaped arm of the imaging device by approximately 90 degrees about the axis; and moving the C-shaped arm along the linear track in a second direction while the source and detector are activated to yield a second elongate image of the object.

Aligning the linear track of the imaging device with the object to be imaged may comprise moving the linear track directly underneath the object to be imaged. Aligning the linear track of the imaging device with the object to be imaged may comprise positioning the linear track parallel to but laterally offset from the object to be imaged. Rotating the C-shaped arm may comprise rotating an arm of the imaging device that secures the C-shaped arm to the linear track from a first position in which the arm is parallel with the linear track to a second position in which the arm is perpendicular to the linear track.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 4A is a top plan view of a line scanner in a first position relative to an imaging table and in a first configuration;

FIG. 4B is a top plan view of the line scanner of FIG. 4A in the first position and a second configuration;

FIG. 4C is a top plan view of the line scanner of FIG. 4A in a second position relative to the imaging table and in the second configuration;

DETAILED DESCRIPTION

Figure 1:
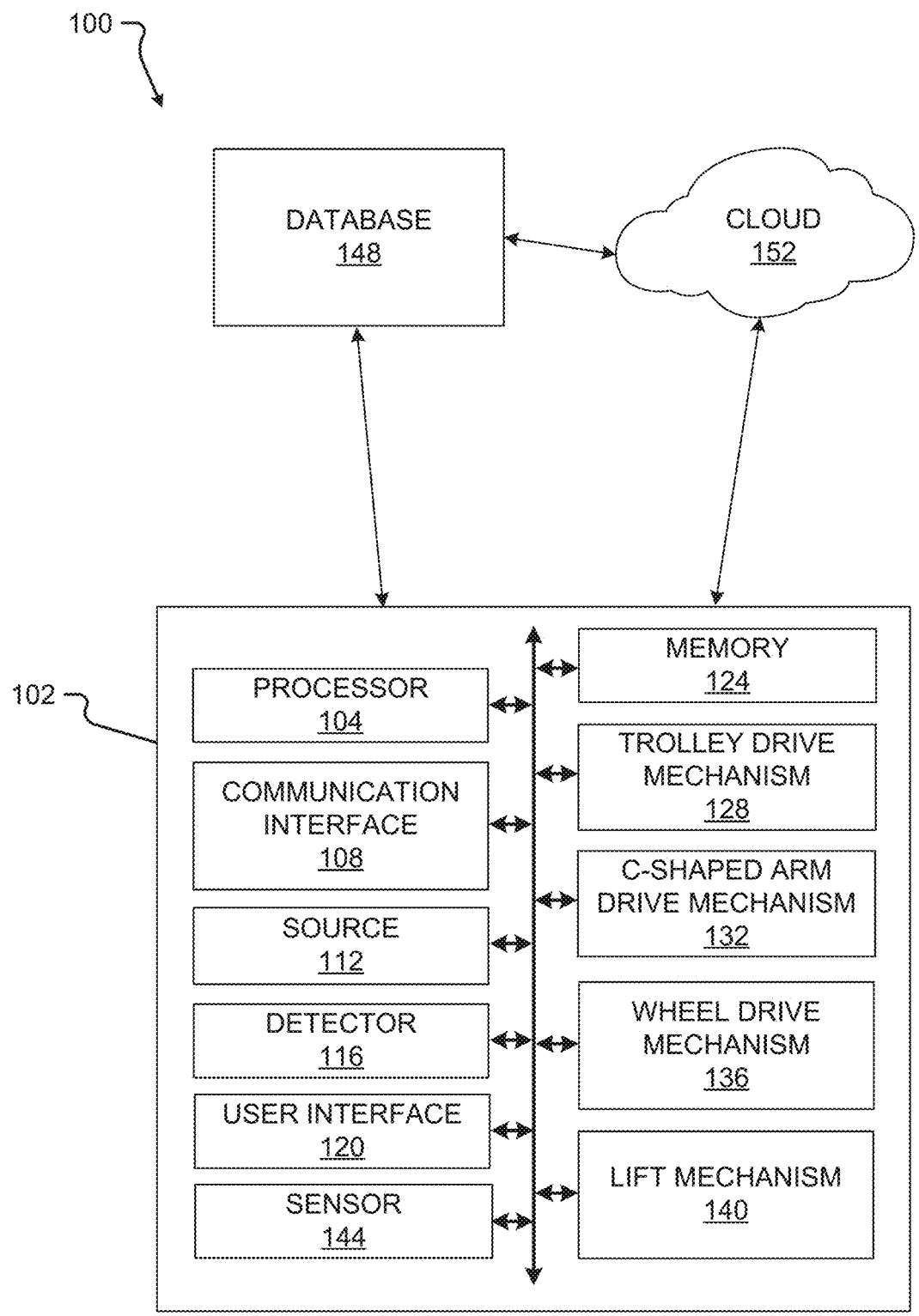
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the methods of this disclosure may be performed by a combination of units or modules associated with, for example, a computing device and/or a medical device (including a medical imaging device).

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Turning first to FIG. 1, a block diagram of a system 100 according to at least one embodiment of the present disclosure is shown. The system 100 may be used to capture long-film image of a patient (including of an anatomical feature of the patient) or an object. In some embodiments, the system 100 may also be used to process, store, and/or display image data associated with the captured image.

The system 100 comprises a line scanner 102, a database 148, and a cloud 152. The line scanner 102 comprises a processor 104, a communication interface 108, a source 112, a detector 116, a user interface 120, a memory 124, a trolley drive mechanism 128, a C-shaped arm drive mechanism 132, a wheel drive mechanism 136, and a sensor 144. Each of these components is described in greater detail below. Systems such as the system 100 according to other embodiments of the present disclosure may comprise more or fewer components than the system 100.

The processor 104 of the line scanner 102 may be any processor described herein or any similar processor. The processor may be configured to execute instructions stored in the memory 124, which instructions may cause the processor to carry out one or more computing steps utilizing or based on data received from or via the communication interface 108, the source 112, the detector 116, the user interface 120, the sensor 144, the database 148, and/or the cloud 152. The one or more computing steps may be steps that control the line scanner 102 to operate in any manner described herein or in any similar manner. The processor 104 may be part of a control system useful for controlling one or more of communication interface 108, the source 112, the detector 116, the user interface 120, the trolley drive mechanism 128, the C-shaped arm drive mechanism 132, the wheel drive mechanism 136, the lift mechanism 140, the sensor 144, and/or any other aspect of the line scanner 102.

The communication interface 108 may be used for receiving image data from the detector 116, for receiving information (including data, instructions, and/or commands) from or via an external source (such as the database 148, and/or the cloud 152), and/or for transmitting images or other information to or via an external source (e.g., the database 148, the cloud 152). The communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, Bluetooth low energy, NFC, ZigBee, and so forth). In some embodiments, the communication interface 108 may be useful for enabling the line scanner 102 to communicate with one or more external processors 104 (either directly or via the cloud 152), whether to reduce the time needed to accomplish a computing-intensive task or for any other reason.

The source 112 may be a source of X-ray or other radiation, and may be configured to emit radiation in a predetermined direction. The radiation may be emitted from the source 112 along a straight line or path or in a fan pattern. The source 112 may be or comprise, for example, an X-ray tube, an X-ray laser, an X-ray generator, a synchrotron, or a cyclotron. The source 112 may be useful for any form of X-ray imaging. In some embodiments, the source 112 may generate low-coherence light useful for optical coherence tomography imaging. In such embodiments, the source 112 may be or comprise for example, one or more superluminescent diodes, ultrashort pulsed lasers, and/or supercontinuum lasers. The source 112 may be transitionable from an inactivated or off state, in which the source 112 does not emit radiation, to an activated or on state, in which the source 112 does emit radiation.

The detector 116 may be any device useful for detecting radiation emitted by the source 112. For example, if the source 112 generates X-ray radiation, then the detector 116 is a device for detecting X-ray radiation. If the source 112 generates low-coherence light, then the detector 116 is a detector for detecting low-coherence light. The size and shape of the detector 116 may be selected to correspond to the path or pattern of radiation emitted by the source 112. For example, if the source 112 emits radiation along a relatively straight, narrow path, then the detector 116 may be configured to detect radiation received along such a path. On the other hand, if the source 112 emits radiation in a fan pattern, then the detector 116 may have a larger size than the source 112 (which size may be based, for example, on how far away from the source 112 the detector 116 will be positioned) and may be correspondingly shaped. In some embodiments, the detector 116 may be positioned directly opposite the source 112, while in other embodiments, the detector 116 may be positioned adjacent the source 112, or in some other relation to the source 112 other than adjacent to or directly opposite the source 112. In some embodiments, the source 112 and the detector 116 are provided in a single device and/or housing (e.g., when the detector 116 is configured to detect radiation bouncing or reflecting off of an object). The detector 116 may be transitionable from an inactivated or off state, in which the detector 116 does not detect radiation, to an activated or on state, in which the detector 116 does detect radiation. The detector 116 may be useful for obtaining or generating image data.

The source 112 and the detector 116 may be secured to a C-shaped arm, as discussed with respect to FIGS. 2A-3B below. In some embodiments, the source 112 and the detector 116 may be replaced by an imaging device or system that does not use one or both of a source 112 or detector 116. For example, in some embodiments of the present disclosure, a camera or other optical sensor may be used instead of the source 112 and the detector 116.

The user interface 120 may be or comprise a keyboard, mouse, trackball, monitor, television, touchscreen, button, joystick, switch, lever, and/or any other device for receiving information from a user and/or for providing information to a user of the line scanner 102. The user interface 120 may be used, for example, to receive a user selection or other user input in connection with aligning an axis of the line scanner 102 with an object to be imaged; to receive a user selection or other user input that causes or otherwise relates to activation of the line scanner 102 to obtain an image; to receive a user selection or other user input regarding one or more configurable settings of the line scanner 102; to receive a user selection or other user input regarding how and/or where to store and/or transfer image data recorded or otherwise obtained by the line scanner 102; and/or to display an image to a user based on image data recorded or otherwise obtained by the line scanner 102.

In some embodiments, the line scanner 102 comprises a plurality of user interfaces 120, which may be identical to each other or different from each other. Although the user interface 120 is shown as part of the line scanner 102, in some embodiments, the line scanner 102 may utilize a user interface 120 that is housed separately from one or more remaining components of the line scanner 102. In some embodiments, the user interface 120 may be located proximate one or more other components of the line scanner 102, while in other embodiments, the user interface 120 may be located remotely from one or more other components of the line scanner 102.

The memory 124 may be or comprise RAM, DRAM, SDRAM, other solid-state memory, any memory described herein, or any other non-transitory memory for storing computer-readable data and/or instructions. The contents of the memory 124 may, in some embodiments, be organized into one or more applications, modules, packages, layers, or engines. The memory 124 may store instructions, information, and/or data useful for completing, for example, any step of the methods 500 and 600 described herein. The memory 124 may store raw data received from the detector 116, processed data generated based on or using the raw data, and any other image data. "Image data," as used herein, refers to any data corresponding to an electronically recorded or generated image—including, for example, data useful for displaying the electronically recorded or generated image on a display device, data regarding one or more parameters of the electronically recorded or generated image, and raw data from which an electronically recorded or generated image is constructed or reconstructed. The memory 124 may be part of a control system useful for controlling one or more of communication interface 108, the source 112, the detector 116, the user interface 120, the trolley drive mechanism 128, the C-shaped arm drive mechanism 132, the wheel drive mechanism 136, the lift mechanism 140, the sensor 144, and/or any other aspect of the line scanner 102.

The line scanner 102 further comprises a trolley drive mechanism 128, which in at least some embodiments comprises one or more motors or other energy conversion devices or systems for selectively causing a trolley of the line scanner 102 to slide along an elongate track, a linear track, an elongate member, a linear member, a rail, or any other elongate or linear component of the line scanner 102. The trolley drive mechanism 128 may be positioned entirely or partially within the trolley, and/or partially within a housing separate from the trolley and connected to the trolley via one or more cables, wires, rods, and/or other force-communication and/or signal-communicating hardware.

In some embodiments, the trolley drive mechanism 128 may also be configured to cause a first portion of the trolley to rotate relative to a second portion of the trolley. For example, a base portion of the trolley may remain in a constant orientation relative to an elongate track of a line scanner 102 (albeit slidably moveable along the elongate track), while the trolley drive mechanism 128 may be configured to selectively cause an upper portion of the trolley to rotate relative to the base portion. The line scanner may comprise a C-shaped arm attached to the upper portion of the trolley, such that rotation of the upper portion of the trolley causes the C-shaped arm to rotate. In some embodiments, the same motor or other energy conversion device of the trolley drive mechanism 128 used to selectively cause the trolley to move along the elongate track may also be used to selectively cause an upper portion of the trolley to rotate relative to a base portion of the trolley. In other embodiments, the trolley drive mechanism 128 may comprise a first mechanism or system for selectively causing the trolley to move along the elongate track, and a second mechanism or system for selectively rotating an upper portion of the trolley relative to a base portion of the trolley.

The trolley drive mechanism 128 may comprise one or more wheels, belts, gears, cables, pulleys, racks, pinions, electromagnets, pistons, rotors, stators, screws, linear motors, worm drives, or other devices for causing linear motion of the trolley along an elongate track and/or for causing an upper portion of the trolley to rotate relative to a base portion of the trolley.

Operation of the trolley drive mechanism 128 may be controlled by the processor 104 and/or by a controller separate from the processor 104. The trolley drive mechanism 128 may be selectively activated to move the trolley into a desired position prior to or following imaging of a patient or object, and/or may be selectively activated to move the trolley during imaging of a patient or object.

The C-shaped arm drive mechanism 132 may comprise one or more electric motors driving one or more gears that are in force-transmitting communication with a C-shaped arm of the line scanner 102. In other embodiments, the C-shaped arm drive mechanism 132 may comprise one or more electric motors driving a belt and wheel/pulley system in force-transmitting communication with the C-shaped arm. In still other embodiments, the C-shaped arm may be part of the C-shaped arm drive mechanism 132. For example, the C-shaped arm drive mechanism 132 may comprise a rotor and a stator, and the rotor may be the C-shaped arm.

The C-shaped arm drive mechanism 132 may, in some embodiments, engage an outer surface or arc of the C-shaped arm, whether with one or more wheels, one or more gears, or otherwise. For example, the C-shaped arm drive mechanism 132 may comprise a motor turning a wheel, which wheel may be pressed against an outer arc or circumferential surface of the C-shaped arm, such that rotation of the wheel causes the C-shaped arm to rotate. In other embodiments, the C-shaped arm may be provided with a plurality of gear teeth along an outer arc or circumferential surface thereof, and the C-shaped arm drive mechanism 132 may comprise a motor turning a gear that engages with the plurality of gear teeth to cause the arcuate arm to rotate.

In other embodiments, the C-shaped arm drive mechanism 132 may engage one or both axial side surfaces or ends of the C-shaped arm. In such embodiments, the C-shaped arm drive mechanism 132 may be or comprise any of the same systems, devices, and components described above, or similar systems, device, and/or components.

Operation of the C-shaped arm drive mechanism 132 may be controlled by the processor 104 and/or by a controller separate from the processor 104. The C-shaped arm drive mechanism 132 may be selectively activated to move the C-shaped arm into a desired position prior to or following imaging of a patient or object, and/or may be selectively activated to cause the C-shaped arm to rotate in between sequential imaging scans of a patient or object. Any motor or other torque-producing device or system, whether electric or otherwise, may be used for the C-shaped arm drive mechanism 132.

The wheel drive mechanism 136 is configured to drive one or more wheels supporting the line scanner 102. The wheel drive mechanism 136 may comprise, for example, one or more motors of other force-producing devices, one or more axles, one or more differentials, one or more gearboxes, and/or any other components useful for powering the wheels. In some embodiments, a separate motor may be connected directly or indirectly to each powered wheel, while in other embodiments, a single motor may generate torque that is transmitted to each powered wheel.

Operation of the wheel drive mechanism 136 may be controlled by the processor 104 and/or by a controller separate from the processor 104. The wheel drive mechanism 136 may be selectively activated to move the line scanner 102 into a desired position prior to or following imaging of a patient or object, and/or may be selectively activated to cause the line scanner 102 to move relative to the patient or object during imaging thereof.

The lift mechanism 140 is configured to selectively raise and lower an elongate track of a line scanner 102, where the elongate track supports a C-shaped arm of the line scanner 102. The lift mechanism 140 may comprise, for example, one or more wheels, belts, gears, cables, pulleys, racks, pinions, electromagnets, pistons, rotors, stators, screws, or other devices for raising and lowering an elongate track. In some embodiments, the lift mechanism 140 comprises two identical mechanisms or systems, located at opposite ends of the elongate track. In other embodiments, the lift mechanism 140 comprises a single mechanism or system positioned entirely at one end of the elongate track, or having one or more components proximate one end of the elongate track and another one or more components proximate an opposite end of the elongate track.

Operation of the lift mechanism 140 may be controlled by the processor 104 and/or by a controller separate from the processor 104. The lift mechanism 140 may be selectively activated to move the line scanner 102 into a desired position prior to or following imaging of a patient or object, and/or may be selectively activated to cause the line scanner 102 to move relative to the patient or object during imaging thereof.

The sensor 144 may be or comprise any sensor useful for determining a position of the line scanner 102 relative to a patient or object to be imaged, and/or relative to a table or other structure supporting a patient or object to be imaged. The sensor 144 may be or comprise, for example, a laser, a linear encoder, an optical sensor, a vision system, a LIDAR system, a RADAR system, a proximity sensor, a location sensor (such as a GNSS sensor (e.g., GPS, GLONASS, Galileo), or an RF sensor for receiving signals that can be used to triangulate a location), and/or any other sensor.

The database 148 may store one or more images taken by one or more imaging devices 102 and may be configured to provide one or more such images (electronically, in the form of image data) to the line scanner 102 (e.g., for display on or via a user interface 120) or to any other device, whether directly or via the cloud 152. In some embodiments, the database 148 may be or comprise part of a hospital image storage system, such as a picture archiving and communication system (PACS), a health information system (HIS), and/or another system for collecting, storing, managing, and/or transmitting electronic medical records including image data.

The cloud 152 may be or represent the Internet or any other wide area network. The line scanner 102 may be connected to the cloud 152 via the communication interface 108, using a wired connection, a wireless connection, or both. In some embodiments, the line scanner 102 may communicate with the database 148 and/or an external device (e.g., a computing device) via the cloud 152.

Figure 2A:
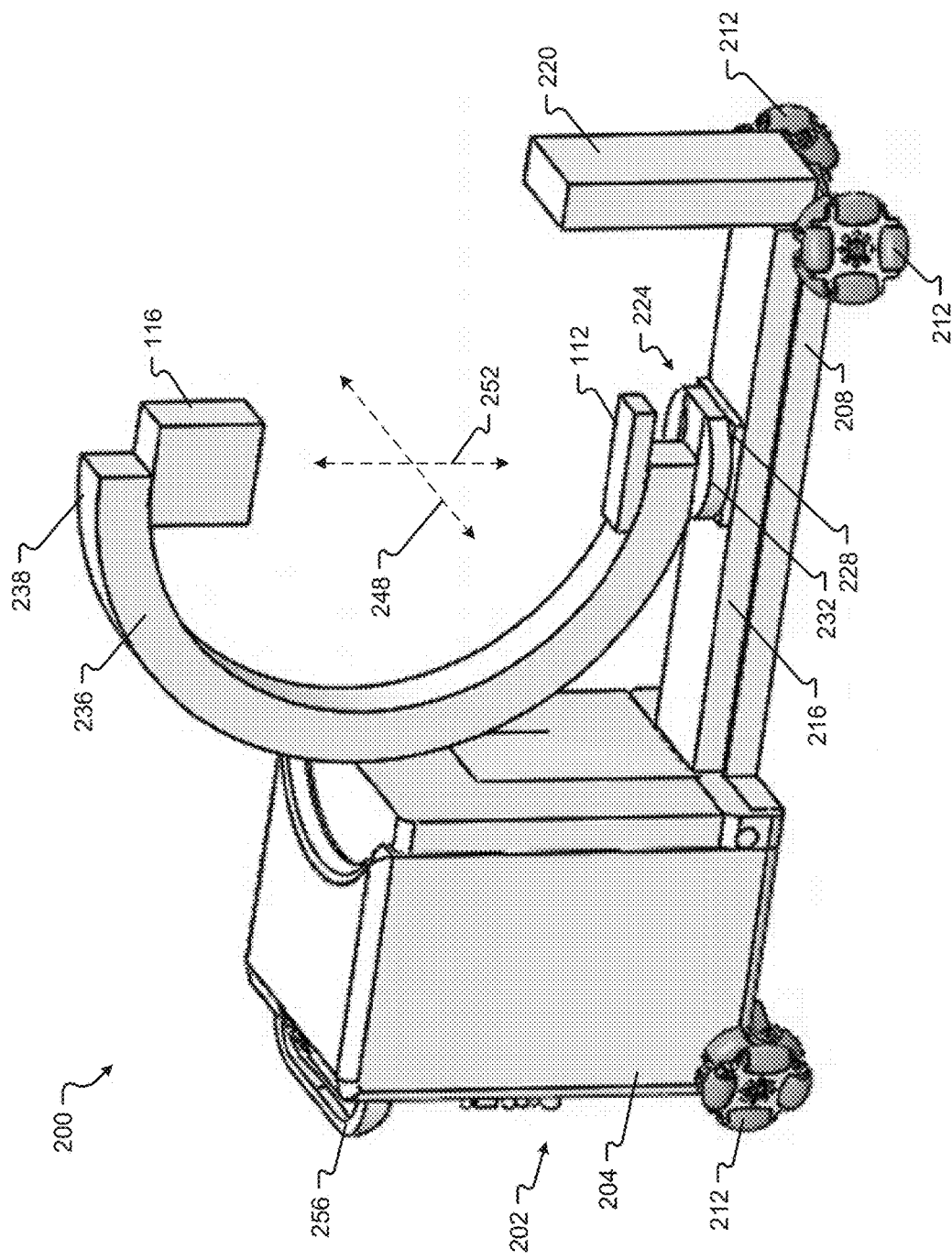
FIG. 2A is a perspective view of a line scanner according to at least one embodiment of the present disclosure, in a first configuration.

FIG. 2A shows a line scanner 200 in a first configuration, which may be referred to as a maneuvering configuration. A line scanner 200 according to embodiments of the present disclosure may comprise some or all of the components of the line scanner 102. The line scanner 200 of FIG. 2A comprises a base 202 (including a housing 204, a base extension 208, and a vertical lift 220), a plurality of wheels 212, an elongate track 216, and a C-shaped arm 236. Each of these components is discussed in more detail below.

The base 202 (including the housing 204, base extension 208, and the vertical lift 220) supports the elongate track 216 and the C-shaped arm 236, and houses various components of the line scanner 200 that are needed to operate and control the line scanner 200. For example, the housing 204 may house a processor 104, a communication interface 108, some or all of a user interface 120, a memory 124, and some or all of a trolley drive mechanism 128, a wheel drive mechanism 136, and/or a lift mechanism 140. The vertical lift 220 may also house some or all of a lift mechanism 140. The elongate track 216 may be supported by the vertical lift 220 and the housing 204 as it is raised and lowered by a lift mechanism 140 between a maximum height and a minimum height (both of which may be defined by the lift mechanism 140, the vertical lift 220 and/or the housing 204). When the elongate track 216 is at the minimum height, the elongate track 216 may rest on the base extension 208. When the elongate track 216 is at the maximum height, the elongate track 216 may be separated from the base extension 208 by a distance of between approximately 6 and 24 inches, or by a distance of between approximately 8 and 20 inches, or by a distance of between approximately 12 and 16 inches. "Approximately" and "about," as used herein and unless otherwise stated, mean within plus or minus ten percent of a stated value.

One or more sensors 144 may, in some embodiments, be mounted to one or more components of the base 202. A handle 256 may be secured to the housing 204 to facilitate manual maneuvering of the line scanner 200. In some embodiments, a user interface 120 may be wholly or partially mounted to and/or supported by the handle 256 or another portion of the housing 204.

The wheels 212 may be omni-directional wheels. One or more of the wheels 212 may be a caster wheel. One or more of the wheels 212 may be the same as or similar to the omni-directional wheels described in U.S. Patent Application Publication No. 2019/0099140 (application Ser. No. 16/144,058) and/or U.S. Patent Application Publication No. 2019/0099141 (application Ser. No. 16/144,103), both filed Sep. 27, 2018 on behalf of applicant Medtronic Navigation, Inc. (referred to hereinafter as the "'140 Publication" and "'141 Publication, respectively), the entirety of each of which is hereby incorporated herein by reference. The wheels 212 may be mounted to the housing 204 via any structure described in the '140 Publication and/or the '141 Publication, or via any other structure suitable for enabling the wheels 212 to support the housing 204.

Additionally, as explained above, one or more of the wheels 212 may be driven via a wheel drive mechanism 136. Where one or more of the wheels 212 is driven, the wheel drive mechanism 136 may be the same as or similar to any drive mechanism described in the '140 Publication and/or the '141 Publication. The wheel drive mechanism 136 may comprise one motor configured to drive one or a plurality of the wheels 212, or a plurality of motors, each configured to drive one or more of the wheels 212. In some embodiments, each driven wheel 212 may be in force-transmitting communication with a separate motor. The wheel drive mechanism 136 may be controlled by one or more user interfaces such as the user interface 120, which may be provided on or near the housing 204 and/or may be separate from but in remote communication with the housing 204 via the communication interface 108.

The wheels 212 may be configured to allow the imaging device 208 to move or be moved forward, backward, sideways, or in any other direction. One or more of the wheels 212 may be selectively lockable. For example, one or more of the wheels 212 may be placed in an unlocked configuration to allow for movement and positioning of the line scanner 200, and in a locked configuration to prevent movement of the line scanner 200 during operation or storage thereof.

The base 202 supports the elongate track 216. The elongate track 216 may alternatively be described as, be, or comprise, for example, a linear track, an elongate member, a linear member, an elongate arm, a linear arm, a rail, a beam, or a rack. The elongate track 216 extends from the housing 204 to the vertical lift 220. In some embodiments, the elongate track 216 has a working length (e.g., a length along which a trolley 224 can move) of greater than about 35 cm, or of at least about 40 cm, or of at least about 50 cm, or of at least about 60 cm. The elongate track 216 may comprise one or more grooves or slots, whether for receiving a protrusion (whether wheeled or otherwise) of the trolley 224 (which protrusion may interact with or be part of the trolley drive mechanism 128, and/or may be configured to slidably secure the trolley 224 to the elongate track 216), or through which a protrusion or other component of the trolley drive mechanism 128 may extend to engage the trolley 224. Similarly, the elongate track 216 may be or comprise one or more rails or other elongate protrusions along which the trolley 224 can roll or slide, or that may be received by one or more grooves in the trolley 224 (e.g., to slidably secure the trolley 224 to the elongate track 216).

As discussed above, the elongate track 216 may be raised or lowered by a lift mechanism 140. In some embodiments, the lift mechanism is partially or entirely disposed in the housing 204 and/or the vertical lift 220, and is configured to impose an upward and/or downward force on the ends of the elongate track 216 to cause the elongate track 216 to rise or fall, respectively. In other embodiments, the ends of the elongate track 216 may be configured to slidably engage the housing 204 and/or the vertical lift 220, but the lift mechanism 140 may be partially or entirely disposed in the base extension 208. For example, the lift mechanism 140 may comprise a scissor lift positioned in between the base extension 208 and the elongate track 216, or one or more pistons positioned in between the base extension 208 and the elongate track 216. In such embodiments, the lift mechanism 140 may impose an upward and/or downward force along a length of the elongate track 216, and the sliding engagement of the ends of the elongate track 216 with the housing 204 and/or the vertical lift 220 may simply assist in maintaining proper alignment of the elongate track 216 while the elongate track 216 is in the raised position.

In still further embodiments of the present disclosure, the elongate track 216 may not engage the housing 204 and/or the vertical lift 220 at all. In such embodiments, the housing 204 and/or the vertical lift 220 may simply prevent the ends of the elongate track 216 from inadvertently snagging or otherwise interfering or being interfered with by an object positioned proximate the line scanner 200.

Also in some embodiments, the base extension 208 and the elongate track 216 may be configured to selectively extend or retract. For example, the base extension 208 and the elongate track 216 may each be provided with a plurality of telescoping members configured to enable the base extension 208 and the elongate track to transition from a maneuvering configuration to an operating configuration. The maneuvering configuration may beneficially have a shorter length to facilitate easy maneuvering of the line scanner 200, while the operating configuration may beneficially have a longer length to enable the line scanner 200 to obtain long-film images of an appropriate length. In the maneuvering configuration, a length of the base extension 208 and the elongate track may be, for example, less than about 35 cm, or less than about 40 cm, or less than about 50 cm. In the operating configuration, a length of the base extension 208 and the elongate track may be, for example, more than about 35 cm, or more than about 40 cm, or more than about 50 cm, or more than about 60 cm. As another example, the base extension 208 and the elongate track 216 may be configured to fold into a maneuvering configuration and unfold into an operating position.

The trolley 224 is secures the C-shaped arm 236 to the elongate track 216, and is itself slidably secured to both the C-shaped arm 236 and the elongate track 216. The trolley 224 may comprise a base portion 228 and an upper portion 232. The base portion 228 is configured to slide, roll, or otherwise move along the elongate track 216, driven by the trolley drive mechanism 128. The base portion 228 is also configured to engage or to be engaged by the elongate track 216, so as to secure the trolley 224 to the elongate track 216.

The upper portion 232 may be rotatably mounted to the base portion 228 of the trolley 224 (e.g., so as to rotate about the axis 252). The upper portion 232 may be configured to rotate at least 90° relative to the base portion 228, or at least 180° relative to the base portion 228, or 360° relative to the base portion 228. The trolley drive mechanism 128 may control rotation of the upper portion 232 relative to the base portion 228 as well as movement of the base portion 228 (and thus of the entire trolley 224) relative to the elongate track 216. The upper portion 232 may be rotatable from a maneuvering position, in which the C-shaped arm supported by the trolley 224 is co-planar with the elongate track 216 (as shown in FIG. 2A), to an operating position, in which the C-shaped arm defines a plane that is perpendicular to the elongate track 216.

The upper portion 232 is also configured to slidably engage an outer circumference or arc 238 of the C-shaped arm 236, so that the C-shaped arm drive mechanism 132 can cause the C-shaped arm 236 to rotate about the C-shaped arm axis 248. The upper portion 232 may be configured to grip one or two flanges extending axially (e.g., parallel to the axis 248) from one or both axial sides of C-shaped arm 236. The upper portion 232 may be configured to grip the axial side surfaces of the C-shaped arm 236. In some embodiments, the upper portion 232 may comprise one or more projections configured to extend into one or more slots on one or more surfaces of the C-shaped arm 236, so as to grip the C-shaped arm 236 entirely or partially from inside the C-shaped arm 236.

Figure 2B:
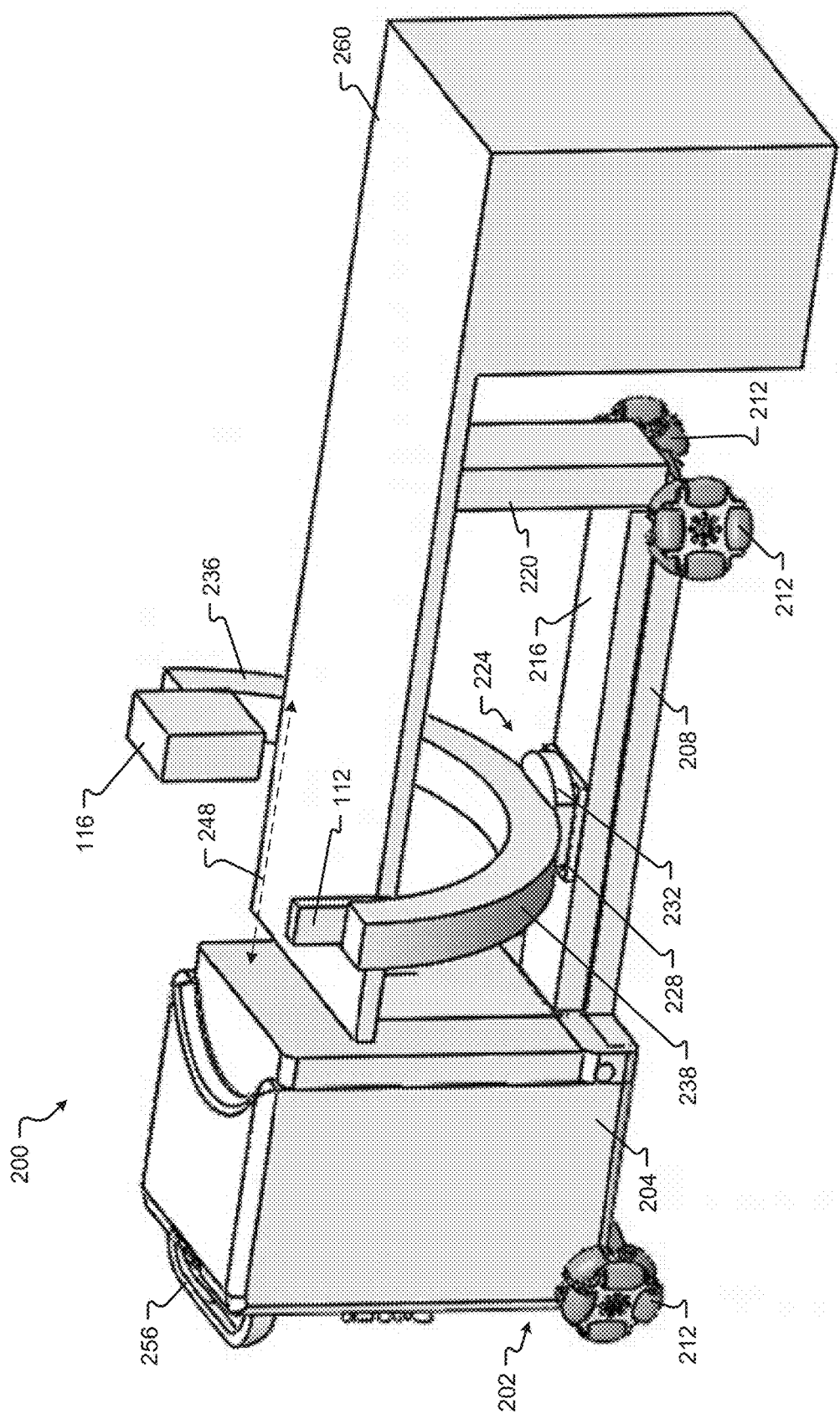
FIG. 2B is a perspective view of the line scanner of FIG. 2A, in a second configuration.

The upper portion 232 may house some or all of the C-shaped arm drive mechanism 132 configured to selectively rotate the C-shaped arm 236 about the axis 248. The C-shaped arm drive mechanism 132 may be configured to rotate the C-shaped arm 236 from a vertical position, in which the upper portion 232 grips the C-shaped arm 236 proximate one end thereof (as shown in FIG. 2A), to a horizontal position, in which upper portion 232 grips the C-shaped arm 236 approximately equidistant between the ends thereof (as shown in FIG. 2B). The C-shaped arm drive mechanism 132 may be configured to rotate the C-shaped arm 236 about 90° relative to the axis 248, so as to transition the C-shaped arm 236 from the vertical position to the horizontal position and vice versa. In some embodiments, the C-shaped arm drive mechanism 132 may be configured to rotate the C-shaped arm 236 about 180° relative to the axis 248, so as to transition the C-shaped arm 236 from the vertical position with the source 112 positioned proximate the elongate track 216, through the horizontal position, and to a vertical position with the source 112 positioned distal the elongate track 216 and the detector 116 positioned proximate the elongate track 216, and vice versa.

The line scanner 200 may be configured to image a patient with the C-shaped arm 236 in the vertical position (e.g., to obtain an anterior-posterior image, whether with the source 112 proximate the elongate track 216 or distal the elongate track 216) and in the horizontal position (e.g., to obtain a lateral image).

The C-shaped arm 236 may comprise an arcuate structure extending through an angular distance of 180° or more around the axis 248. The C-shaped arm 236 supports the source 112 and the detector 116, each of which is fixedly secured to the C-shaped arm 236 and are separated from each other by an angular distance of approximately 180°, as measured around the axis 248 (e.g., from a center of the source 112 to a center of the detector 116). In some embodiments, a different imaging device or system may be utilized by the line scanner 200. In such embodiments, the different imaging device or system may be secured at one or more positions of the C-shaped arm 236 suitable to enable proper operation of the different imaging device or system.

FIG. 2B illustrates the line scanner 200 in a second configuration, which may be referred to as an operating configuration. In FIG. 2B, the C-shaped arm 236 has been rotated by the upper portion 232 (and more specifically, by the trolley drive mechanism 128) into a plane that is perpendicular to the elongate track 216, and has further been rotated into the horizontal position by the C-shaped arm drive mechanism 132. In the configuration shown in FIG. 2B, the axis 248 of the C-shaped arm 236 is aligned with the imaging table 260 (which may be, for example, an operating table). If a patient were laying along and aligned with the imaging table 260, the axis 248 of the C-shaped arm 236 would be extending through the patient in the superior-inferior direction. In this configuration, the C-shaped arm 236 is prepared to obtain a long-film lateral image of an anatomical feature of the patient (e.g., of the patient's spine). More specifically, the long-film lateral image would be obtained by activating the source 112 and the detector 116, and causing the trolley 224 to move along the elongate track 216 toward the vertical lift 220. Similarly, the line scanner 200 may be configured to obtain a long-film anterior-posterior image of an anatomical feature of the patient (e.g., of the patient's spine) by rotating the C-shaped arm 236 into the vertical position, then activating the source 112 and the detector 116 and causing the trolley 224 to move along the elongate track 216 toward the vertical lift 220.

Notably, the line scanner 200 may obtain long-film images of an anatomical feature of the patient (or of any other object aligned with the axis 248 of the C-shaped arm 236) by activating the source 112 and the detector 116 and moving trolley 224 (and thus the C-shaped arm 236) either from proximate the housing 204 to proximate the vertical lift 220, or from proximate the vertical lift 220 to proximate the housing 204.

Figure 3A:
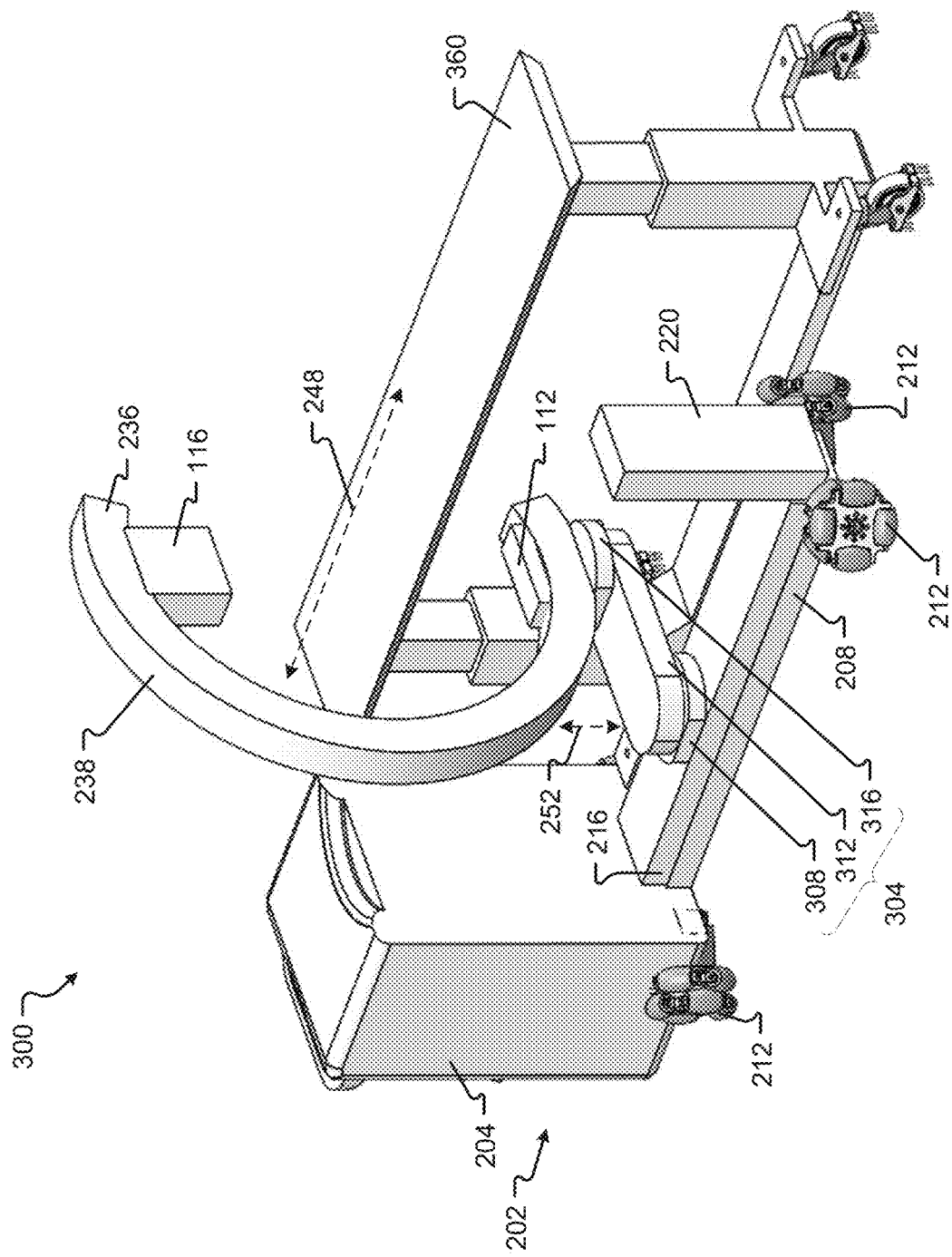
FIG. 3A is a perspective view of another line scanner according to at least one embodiment of the present disclosure, in a first configuration.
Figure 3B:
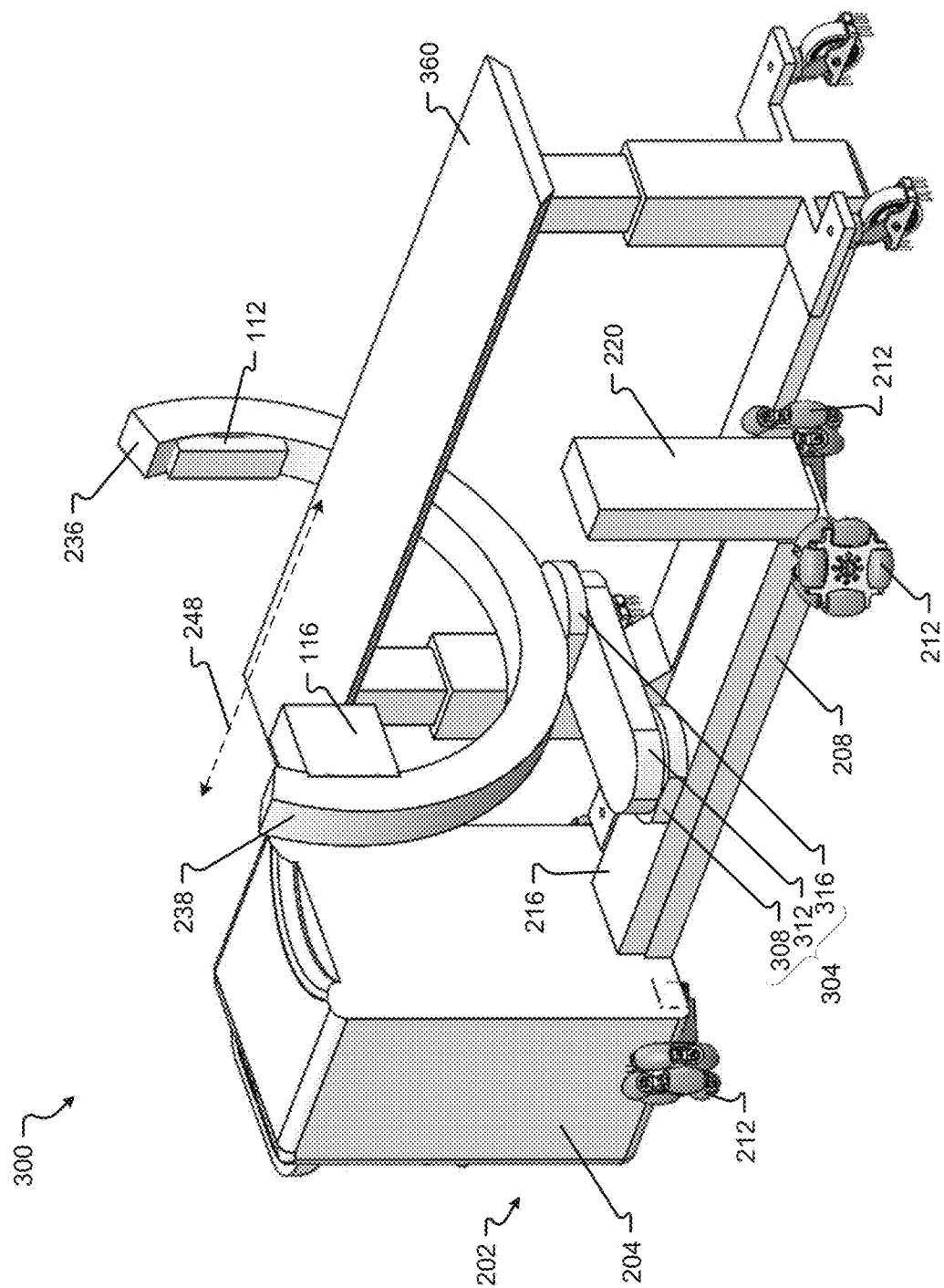
FIG. 3B is a perspective view of the line scanner of FIG. 3A, in a second configuration.

FIGS. 3A-3B illustrate a line scanner 300 that is substantially similar to the line scanner 200, including in that the line scanner 300 comprises: a base 202 that includes a housing 204, a base extension 208, and a vertical lift 220; a plurality of wheels 212; an elongate track 216; and a C-shaped arm 236 having an axis 248 and supporting a source 112 and a detector 116. As in FIGS. 2A-2B, the elongate track 216 of FIGS. 3A-3B may be elevated relative to the base extension 208, so as to raise the axis 248 of the C-shaped arm 236 to a higher position (e.g., to properly position the C-shaped arm 236 to image a patient or object placed on the imaging table 360). The line scanner 300 differs from the line scanner 200 in two ways: first, the C-shaped arm 236 of the line scanner 300 extends through an arc of greater than 180°; and second, the line scanner 300 comprises a trolley 304 rather than a trolley 224.

The trolley 304 comprises a base portion 308, an arm 312, and an upper portion 316. The upper portion 232 of the trolley 224 is configured to rotate the C-shaped arm 236 about the axis 252, and therefore enables the line scanner 200 to image a patient or object on an imaging table 260 when a portion of the line scanner 200 is positioned directly underneath and substantially aligned with a longitudinal centerline of the imaging table 260. In contrast, the trolley 304 enables the line scanner 300 to properly position the C-shaped arm 236 to image a patient or object on an imaging table 360 when the line scanner 300 is parallel with but offset from a longitudinal centerline of the table 360, and thus is not directly underneath the table 360.

More specifically, the arm 312 of the trolley 304 is configured to rotate relative to the base portion 308, into a position that is approximately perpendicular to the elongate track 216. The arm 312 may be configured to rotate, for example, about 90° relative to the base portion 308. In some embodiments, the arm 312 may be configured to rotate more than about 90° relative to the base portion 308. Also in some embodiments, the arm 312 may comprise two or more linkages, so that the arm 312 can be folded to a relatively small length when not in use, and extended to a longer length during operation.

When the arm 312 is rotated as described above, the upper portion 316 is no longer positioned directly over the base portion 308 or any portion of the elongate track 216. Because rotation of the arm 312 has a more significant impact on the center of gravity of the line scanner 300 than does rotation of the upper portion 232 of the trolley 224 on the center of gravity of the line scanner 200, the line scanner 300 may have a wider wheel base than the line scanner 200, and/or may comprise extendable supports to temporarily widen the base 202 of the line scanner 300 while the arm 312 is in the rotated position.

The upper portion 316 may be fixedly secured to the arm 312, but like the upper portion 232, the upper portion 316 is configured to slidably engage an outer circumference or arc 238 of the C-shaped arm 236, so that the C-shaped arm drive mechanism 132 can cause the C-shaped arm 236 to rotate about the C-shaped arm axis 248. Also like the upper portion 232, the upper portion 316 may house some or all of the C-shaped arm drive mechanism 132 configured to selectively rotate the C-shaped arm 236 about the axis 248.

As may be appreciated in light of the foregoing disclosure, the line scanners 200 and 300 are configured to maneuver the C-shaped arm 236 in a plurality of ways: by raising and lowering the C-shaped arm 236 (by raising and lowering the elongate track 216); by sliding the C-shaped arm along the elongate track 216 (by moving the trolley 224 or the trolley 304 along the elongate track 216); by rotating the C-shaped arm about the axis 252 (for the line scanner 200); by rotating the arm 312 about the axis 252 (for the line scanner 300); and by rotating the C-shaped arm 236 about the axis 248. Further movement of the C-shaped arm 236 is possible by maneuvering the base 202 in any direction, whether during one or more of the movements described above or not.

Although the line scanners 200 and 300 are described as having various drive mechanisms for the various forms of maneuvering identified above (any of which may be automatically operable or operable under control of a user), in some embodiments, the line scanner 200 and/or the line scanner 300 may be configured for manual operation. For example, a line scanner 200 and/or 300 may comprise a crank or other manually operated lift for raising and lowering the elongate track 216. Similarly, a line scanner 200 and/or 300 (as appropriate) may be configured for manual rotation of the C-shaped arm about the axis 252, of the arm 312 about the axis 252, and/or of the C-shaped arm 236 about the axis 248. Further, a line scanner 200 and/or 300 may be configured for manual movement of the trolley/C-shaped arm along the elongate track 216.

Both the line scanner 200 and the line scanner 300 beneficially retain the ability to be returned to a relatively small form factor when not in use (e.g., by lowering the elongate track 216 to a minimum level and rotating the C-shaped arm 236 so that it is in the vertical position and so that it is co-planar with the elongate track 216). In this position, the line scanners 200 and 300 may be maneuvered much more easily than a conventional O-arm, including due to improved visibility for a person maneuvering the line scanner 200 or 300 and due to a slimmer profile that is less likely to catch, snag, or otherwise collide with an object around which the line scanner 200 or 300 is being maneuvered.

FIGS. 4A-4F illustrate a potential sequence of operations for a line scanner 300, which might be performed to obtain both anterior-posterior and lateral long-film line scans of, for example, a spine of a patient (not shown) positioned on the imaging table 360. The long-film line scans may have a length, for example, of about 40 cm, or about 50 cm, or about 60 cm.

As shown in FIG. 4A, the line scanner 300 is maneuvered to a position adjacent to and parallel with the imaging table 360. The maneuvering may be accomplished manually by an operator, or automatically by the processor 104 executing instructions stored in the memory 124, based on information received from one or more sensors 144, to control a wheel drive mechanism 136. In some embodiments, an operator may use a wired or wireless controller or other user interface to provide commands to the line scanner 300 and thus control a wheel drive mechanism 136, so as to effectively drive the line scanner 300 into a desired position. The maneuvering may be aided by the use of castered or omni-directional wheels 212 as described above. During such movements, the line scanner 300 is in a storage position (e.g., with the C-shaped arm 236 co-planar with the elongate track 236 and in the vertical position, and the elongate track 216 lowered to a minimum level).

As shown in FIG. 4B, the line scanner 300 is extended into an operating position by rotating the arm 312 to a position substantially perpendicular to the elongate track 216. If necessary, the elongate track 216 (and thus the C-shaped arm 236) may be raised to an appropriate height for imaging the patient's spine (e.g., using a lift mechanism 140).

As shown in FIG. 4C, the line scanner 300 is then maneuvered toward the imaging table 360. Here again, movement of the line scanner 300 may be facilitated by the use of castered or omnidirectional wheels.

Figure 4F:
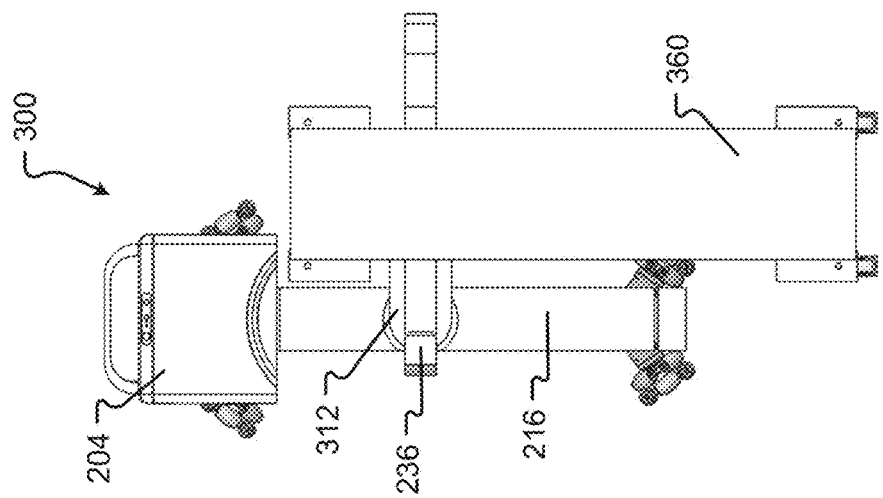
FIG. 4F is a top plan view of the line scanner of FIG. 4A in the second position and a fifth configuration.
Figure 4E:
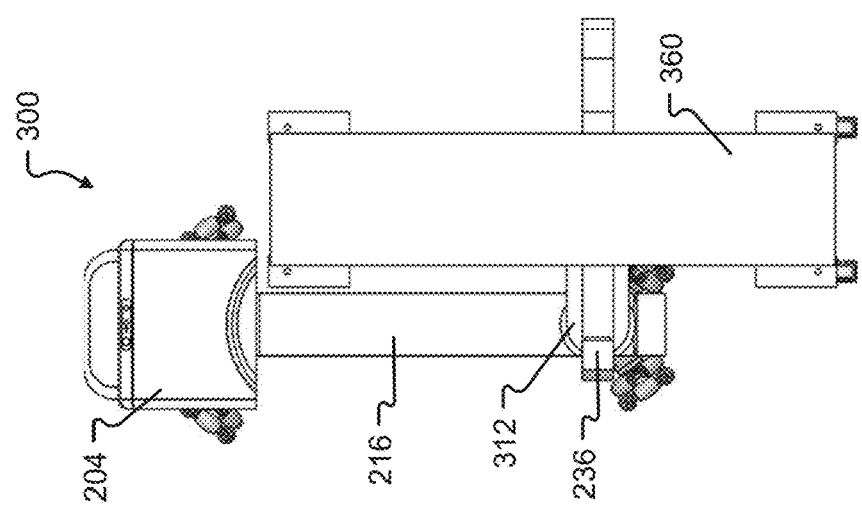
FIG. 4E is a top plan view of the line scanner of FIG. 4A in the second position and a fourth configuration.
Figure 4D:
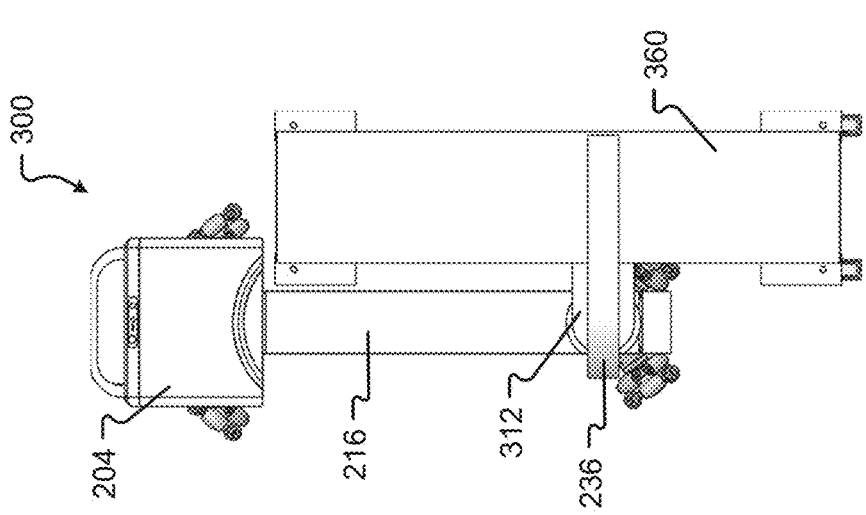
FIG. 4D is a top plan view of the line scanner of FIG. 4A in the second position and a third configuration.

As shown in FIG. 4D, the C-shaped arm 236 is moved along the elongate track 216 (e.g., by moving the trolley 304 with the trolley drive mechanism 128) to obtain an anterior-posterior long-film line scan. During this movement, the source 112 and the detector 116 are activated. The distance traveled by the C-shaped arm 236 corresponds to the length of the desired long-film line scan (e.g., about 40 cm, or about 50 cm, or about 60 cm).

As shown in FIG. 4E, the C-shaped arm 236 may be rotated about its axis 248 into a horizontal position to obtain a lateral long-film line scan of the patient's spine. The rotation may be accomplished using a C-shaped arm drive mechanism 132.

As shown in FIG. 4F, the C-shaped arm 236 is again moved along the elongate track 216 (e.g., by moving the trolley 304 with the trolley drive mechanism 128) to obtain a lateral long-film line scan. During this movement, which may be in an opposite direction from the movement described with respect to FIG. 4D, the source 112 and the detector 116 are activated. Here again, the distance traveled by the C-shaped arm 236 corresponds to the length of the desired long-film line scan (e.g., about 40 cm, or about 50 cm, or about 60 cm).

As is evident from FIGS. 4A-4F, the elongate track 216 and base extension 208 may need to be longer than a desired length of travel of the C-shaped arm 236, to ensure that the C-shaped arm 236 can travel the desired length of the long-film line scan without interference from the imaging table 360. Additionally, the housing 204 may prevent a line scanner 200 or 300 from being maneuvered as close to an imaging table 260 or 360 as necessary to enable the C-shaped arm 236 to achieve the desired length of travel along an anatomical feature of interest of a patient. (In FIGS. 4A-4F, for example, the housing 204 must remain beyond an end of the imaging table 360 to enable the elongate track 216 to be maneuvered as close to the imaging table 360 as necessary for the C-shaped arm 236 to be properly positioned relative to the imaging table 360). Again, this issue may be addressed by providing a base extension 208 and/or an elongate track 216 of sufficient length to extend past any unusable space and still enable the C-shaped arm 236 to travel the length of the desired long-film line scan.

Although not shown, the present disclosure also encompasses long-film line scanners that utilize a multi jointed robotic arm attached to a base (which may be similar, for example, the base 202, although an elongate track such as the elongate track 216 may or may not be needed) and holding a C-shaped arm such as the C-shaped arm 236 with a C-shaped arm drive mechanism such as the C-shaped arm drive mechanism 132. In such embodiments, the long-film line scanner may obtain a long-film line scan of a desired length by using the robotic arm to maneuver the C-shaped arm along a linear path, both in a horizontal position and in a vertical position. Line scanners according to such embodiments may not utilize an elongate track 216, a trolley 224 or 334, a vertical lift 220, a trolley drive mechanism 128, and/or a lift mechanism 140. However, line scanners according to such embodiments may still utilize a processor 104, a communication interface 108, a source 112, a detector 116, a user interface 120, a memory 124, a C-shaped arm drive mechanism 132, a wheel drive mechanism 136, and/or a sensor 144, and may still comprise a housing 204, a plurality of wheels 212, and a C-shaped arm 236.

Figure 5:
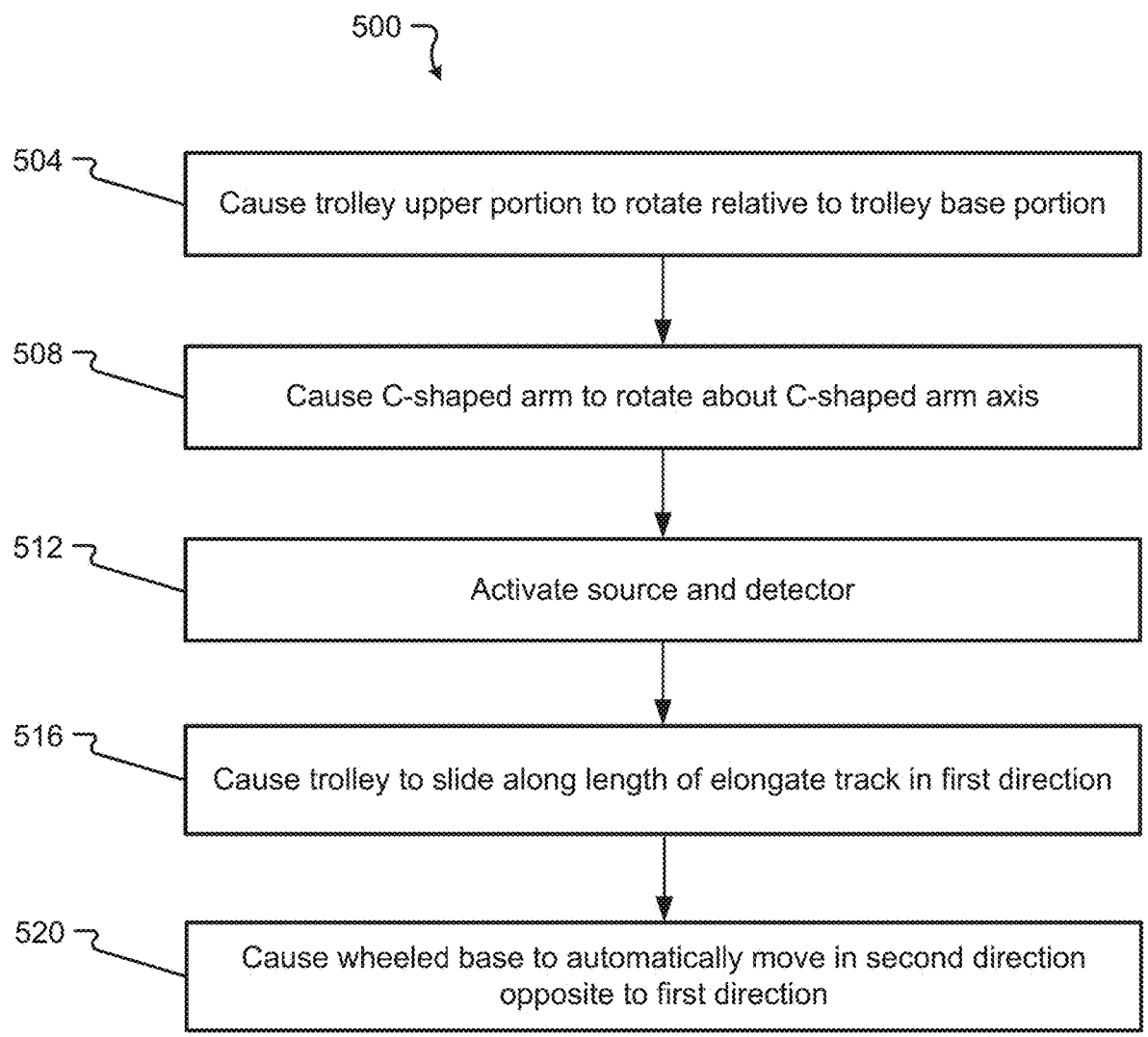
FIG. 5 is a flowchart of a method according to at least one embodiment of the present disclosure.

Turning now to FIG. 5, a method 500 of obtaining a long-film line scan using a line scanner according to some embodiments of the present disclosure comprises causing a trolley upper portion to rotate relative to a trolley base portion (step 504). The trolley upper portion may the same as or similar to the upper portion 232 or 316, and the trolley base portion may be the same as or similar to the base portion 228 or 308. The trolley upper portion and the trolley lower portion may be included in a trolley such as the trolley 224 or the trolley 304. The trolley upper portion may rotate relative to the trolley base portion around an axis such as the axis 252. Rotation of the trolley upper portion relative to the trolley base portion may result in a C-shaped arm supported by the trolley upper portion being rotated from a first position, in which the C-shaped arm is coplanar with an elongate track to which the trolley lower portion is slidably connected, to a second position, in which the C-shaped arm defines a plane that is perpendicular to such an elongate track. The rotation of the trolley upper portion relative to the trolley base portion may be accomplished, for example, using a trolley drive mechanism such as the trolley drive mechanism 128.

The method 500 also comprises causing a C-shaped arm to rotate about an axis defined by the C-shaped arm (step 508). The rotation may have an angular distance of about 90°. The rotation may be accomplished using a C-shaped arm drive mechanism such as the C-shaped arm drive mechanism 132. The rotation may result in the C-shaped arm transitioning from a vertical position to a horizontal position, or from a horizontal position to a vertical position.

The method 500 also comprises activating a source and a detector (step 512). The source and the detector may each be fixedly secured to the C-shaped arm. The source may be the same as or similar to the source 112, and the detector may be the same as or similar to the detector 116. Activation of the source and the detector may enable the source and detector to obtain and/or generate a long-film line scan (e.g., as the C-shaped arm to which the source and the detector are fixedly secured is moved along an elongate track).

The method 500 also comprises causing a trolley to slide along a length of an elongate track in a first direction (step 516). The trolley may comprise the trolley upper portion and the trolley lower portion described above, and may be the same as or similar to the trolley 224 or the trolley 304. The elongate track may have a length of at least about 40 cm, or about 50 cm, or about 60 cm. The elongate track may be the same as or similar to the elongate track 216. The elongate track may be vertically positionable, e.g., using a lift mechanism such as the lift mechanism 140. A trolley drive mechanism such as the trolley drive mechanism 128 may be used to cause the trolley to slide along the length of the elongate track.

The distance that the trolley slides along the elongate track may correspond to a desired length of a long-film line scan of a patient or object being imaged. For example, the trolley may slide about 40 cm, or about 50 cm, or about 60 cm along the elongate track. The first direction may be in a direction from proximate a housing 204 to proximate a vertical lift 220, or in a direction from proximate a vertical lift 220 to proximate a housing 204.

The method 500 also comprises causing a wheeled base to automatically move in a second direction opposite to the first direction (step 520). The wheeled base may be the same as or similar to the base 202. The wheeled base may comprise a plurality of wheels such as the wheels 212, which may be omnidirectional or castered wheels. The wheeled base may comprise a wheel drive mechanism 136 that is used to automatically move the wheeled base in a second direction opposite to the first direction. The movement of the wheeled base in the second direction may occur at the same speed that the trolley slides along the elongate track in the first direction, such that relative to an object being imaged or any other fixed reference (e.g., an imaging table 260 or 360), the trolley (and a C-shaped arm supported by the trolley) remains motionless. Movement of the wheeled base in the second direction may be accomplished, for example, to return the line scanner to a storage position after imaging of a patient or object, or to place the line scanner in an operating position prior to imaging of a patient or object.

Figure 6:
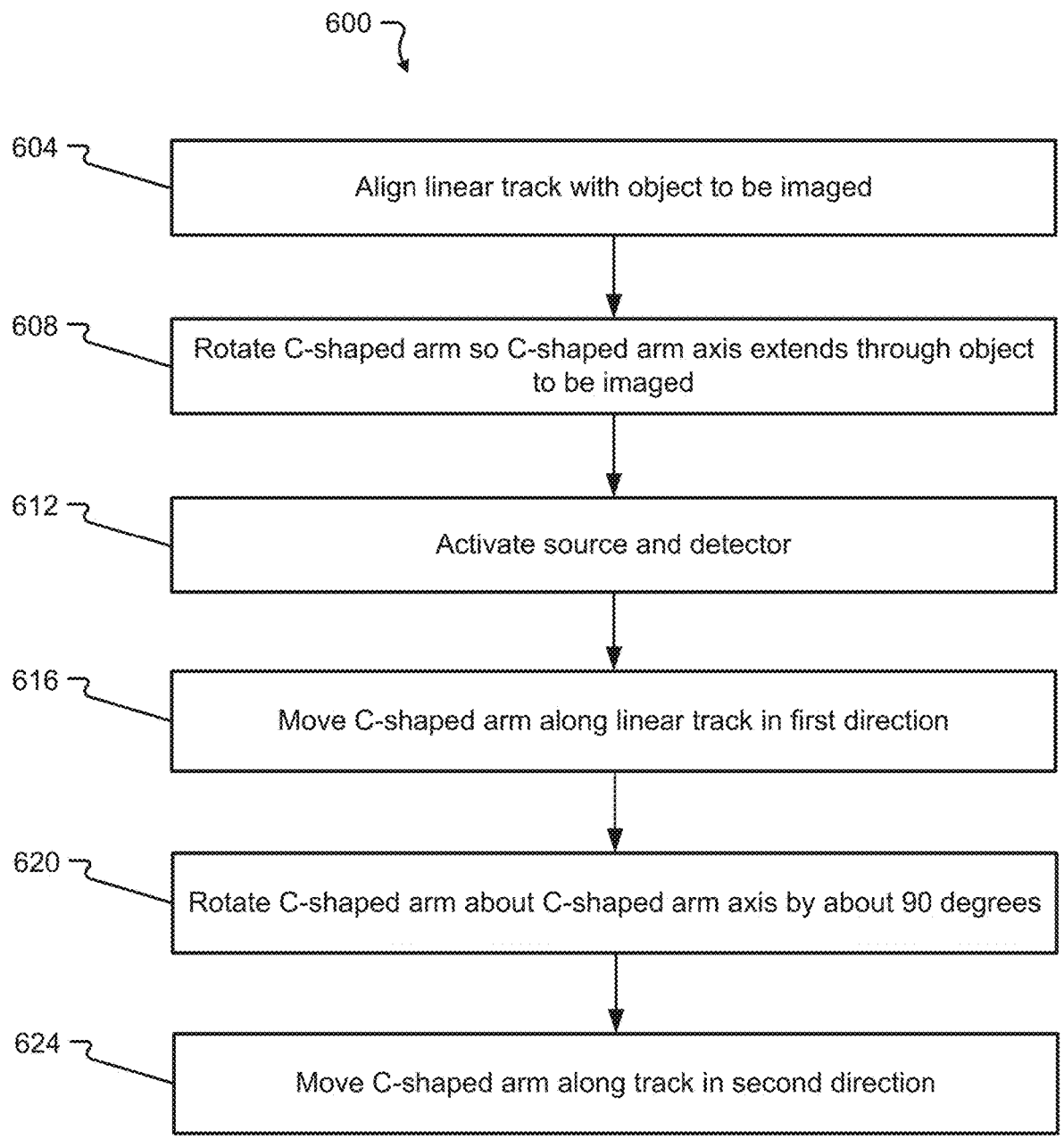
FIG. 6 is a flowchart of another method according to at least one embodiment of the present disclosure.

With reference now to FIG. 6, a method 600 of obtaining a long-film line scan using a line scanner according to some embodiments of the present disclosure comprises aligning a linear track of a long-film line scanner such as the line scanner 200 or 300 with an object to be imaged (step 604). The aligning may occur in the same manner or in a similar manner to the maneuvering described above with respect to FIG. 4A. The aligning may result in the linear track being positioned directly underneath an object to be imaged (e.g., as shown in FIG. 2B) or in the linear track being positioned adjacent an object to be imaged (e.g., as shown in FIG. 3A). The aligning may occur automatically (e.g., using a processor such as the processor 104, executing instructions stored in a memory such as the memory 124 and based on information received from one or more sensors 144, to control a wheel drive mechanism such as the wheel drive mechanism 136) or manually.

The method 600 further comprises rotating a C-shaped arm so that the C-shaped arm axis extends through the object to be imaged (step 608). The C-shaped arm may be the same as or similar to the C-shaped arm 236. The rotation may be accomplished, for example, by rotating an upper portion of a trolley (such as the upper portion 232 or 316 of the trolley 224 or 304) relative to a base portion of the trolley (such as the base portion 228 or 308). The rotation may be accomplished by rotating an arm such as the arm 312 of the trolley 304 relative to a base portion such as the base portion 308. The rotation may be through an angular distance of approximately 90°.

The rotation causes the C-shaped arm axis to extend through the object to be imaged along a direction in which a long-film line scan is to be taken. For example, if a long-film line scan is to be taken of a patient's spine, then the C-shaped arm axis, once the C-shaped arm is rotated, may extend through the patient and substantially parallel to the spine (e.g., through the patient in a superior-inferior direction).

The method 600 further comprises activating a source and a detector fixedly secured to the C-shaped arm (step 612). The source may be the same as or similar to the source 112, and the detector may be the same as or similar to the detector 116. Activation of the source and the detector may enable the source and detector to obtain and/or generate a long-film line scan (e.g., as the C-shaped arm to which the source and the detector are fixedly secured is moved along a linear track).

The method 600 further comprises moving the C-shaped arm along the linear track in a first direction (step 616). The movement may be accomplished by causing a trolley such as the trolley 224 or the trolley 304 to move along the linear track (e.g., using a trolley drive mechanism such as the trolley drive mechanism 128). The linear track may have a working length of at least about 40 cm, or about 50 cm, or about 60 cm. The linear track may be the same as or similar to the elongate track 216. The linear track may be vertically positionable, e.g., using a lift mechanism such as the lift mechanism 140. The movement of the C-shaped arm along the linear track in the first direction may occur, for example, while the source and the detector are activated (e.g., to obtain a long-film line scan of an anatomical feature of a patient or another object), or while the source and the detector are not activated (e.g., to reposition the C-shaped arm in preparation for obtaining a long-film line scan or for storage).

The distance that the C-shaped arm moves along the linear track may correspond to a desired length of a long-film line scan of a patient or object being imaged. For example, the C-shaped arm may be moved about 40 cm, or about 50 cm, or about 60 cm along the linear track. The first direction may be in a direction from proximate a housing 204 to proximate a vertical lift 220, or in a direction from proximate a vertical lift 220 to proximate a housing 204.

The method 600 further comprises rotating the C-shaped arm about the C-shaped arm axis by about 90 degrees (step 620). The rotation may be accomplished using a C-shaped arm drive mechanism such as the C-shaped arm drive mechanism 132. The rotation may result in the C-shaped arm transitioning from a vertical position to a horizontal position, or from a horizontal position to a vertical position.

The method 600 further comprises moving the C-shaped arm along the track in a second direction opposite the first direction (step 624). The moving the C-shaped arm along the track in the second direction may be accomplished in substantially the same manner as the moving the C-shaped arm along the linear track in the first direction, except that the C-shaped arm is moved in the second direction opposite the first direction instead. The movement of the C-shaped arm along the linear track in the second direction may occur, for example, while the source and the detector are activated (e.g., to obtain a long-film line scan of an anatomical feature of a patient or another object), or while the source and the detector are not activated (e.g., to reposition the C-shaped arm in preparation for obtaining a long-film line scan or for storage).

As may be appreciated based on the foregoing disclosure, the present disclosure encompasses methods with fewer than all of the steps identified in FIGS. 5 and/or 6 and the corresponding description of the methods 500 and 600, as well as methods that include more steps than those identified in FIGS. 5 and/or 6 and the corresponding description of the methods 500 and 600. In some embodiments, one or more steps of the methods 500 and/or 600 may be repeated one or more times.

One or more aspects of a line scanner according to embodiments of the present disclosure may be the same as or similar to one or more aspects of the imaging device(s) described in a patent application filed contemporaneously herewith, by the same applicant, entitled "G-Arm Imaging Device," the entirety of which is hereby incorporated herein by reference. In particular, a line scanner according to embodiments of the present disclosure may be configured to obtain 3D scans (whether long-film or not) of an anatomical feature of a patient and/or an object, using a G-arm as described in the aforementioned reference in place of the C-shaped arm described herein.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An imaging device comprising:
   a wheeled base comprising an elongate track that is extendable along a first axis via a telescoping member;
   a trolley comprising a base portion slidably connected to the elongate track and an upper portion rotatably connected to the base portion, the trolley slidable along the elongate track and along the first axis a distance of at least 40 cm;
   a C-shaped arm defining a semi-circle about a C-shaped arm axis, the C-shaped arm rotatably supported by the upper portion of the trolley, wherein the upper portion of the trolley enables rotation of the C-shaped arm along a rotational axis that is perpendicular to the first axis;
   a source fixedly secured to the C-shaped arm; and
   a detector fixedly secured to the C-shaped arm opposite the source.

2. The imaging device of claim 1, wherein the upper portion is rotatable relative to the base portion about a first axis perpendicular to the elongate track.

3. The imaging device of claim 1, wherein the upper portion is configured to selectively rotate the C-shaped arm about the C-shaped arm axis.

4. The imaging device of claim 1, wherein the trolley further comprises an intermediate arm rotatable between a first position parallel to the elongate track and a second position perpendicular to the elongate track.

5. The imaging device of claim 1, wherein the wheeled base comprises a plurality of omnidirectional wheels.

6. The imaging device of claim 1, wherein the wheeled base comprises:
a plurality of powered wheels; and
a controller for selectively activating the powered wheels to move the wheeled base relative to a stationary object.

7. The imaging device of claim 1, wherein the trolley is slidable along the elongate track a distance of at least 60 cm and wherein the telescoping member increases a length of the wheeled base.

8. The imaging device of claim 1, further comprising:
a processor; and
a memory storing instructions for execution by the processor that, when executed, cause the processor to:
transmit a first signal that causes the upper portion to rotate relative to the base portion;
transmit a second signal that causes the C-shaped arm to rotate about the C-shaped arm axis;
activate the source and the detector; and
transmit a third signal that causes the trolley to slide along a length of the elongate track in a first direction.

9. The imaging device of claim 8, wherein the memory stores additional instructions for execution by the processor that, when executed, further cause the processor to:
transmit a fourth signal that causes the wheeled base to automatically move in a second direction opposite the first direction.

10. The imaging device of claim 1, further comprising a sensor for determining a position of the C-shaped arm relative to a stationary object.

11. An imaging system comprising:
a housing;
an elongate member extending from the housing, wherein the elongate member is extendable in a horizontal axis;
a mount slidably secured to the elongate member;
a C-shaped arm defining a C-shaped arm axis and movably attached to the mount, the C-shaped arm rotatable on the mount about a first axis perpendicular to the horizontal axis and about the C-shaped arm axis, the C-shaped arm comprising an imaging tool; and
a control system configured to selectively cause the mount to slide along the elongate member and the C-shaped arm to rotate relative to the mount, and to selectively activate the imaging tool.

12. The imaging system of claim 11, wherein the housing and the elongate member are supported by a plurality of wheels.

13. The imaging system of claim 12, wherein at least some of the plurality of wheels are powered, and further wherein the control system is further configured to selectively activate the powered wheels.

14. The imaging system of claim 11, wherein the C-shaped arm is movable between a storage configuration, in which the C-shaped arm and the elongate member are co-planar, and an operating position, in which the C-shaped arm defines a first plane and the elongate member defines a second plane perpendicular to the first plane.

15. The imaging system of claim 11, wherein the mount is slidable along the elongate member by a distance of at least 50 cm.

16. A method of operating an imaging device, comprising:
aligning a linear track of an imaging device with an object to be imaged, the object elongated in a longitudinal direction;
extending a length of the linear track in the longitudinal direction;
rotating a C-shaped arm of the imaging device so that an axis defined by the C-shaped arm extends through the object in the longitudinal direction;
activating a source and detector secured to the C-shaped arm; and
moving the C-shaped arm along the linear track in a first direction while the source and detector are activated to yield a first elongate image of the object.

17. The method of claim 16, further comprising:
rotating the C-shaped arm of the imaging device by approximately 90 degrees about the axis; and
moving the C-shaped arm along the linear track in a second direction while the source and detector are activated to yield a second elongate image of the object.

18. The method of claim 16, wherein aligning the linear track of the imaging device with the object to be imaged comprises moving the linear track directly underneath the object to be imaged.

19. The method of claim 16, wherein aligning the linear track of the imaging device with the object to be imaged comprises positioning the linear track parallel to but laterally offset from the object to be imaged.

20. The method of claim 19, wherein rotating the C-shaped arm comprises rotating an arm of the imaging device that secures the C-shaped arm to the linear track from a first position in which the arm is parallel with the linear.

* * * * *